United States Patent [19]

Juby et al.

[11] 4,079,057

[45] Mar. 14, 1978

[54] SELECTIVE IMMUNOSUPPRESSIVE AGENTS

[75] Inventors: Peter Frederick Juby, Jamesville; Thomas William Hudyma, Manlius, both of N.Y.

[73] Assignee: Bristol-Myers Company, New York, N.Y.

[21] Appl. No.: 801,491

[22] Filed: May 31, 1977

[51] Int. Cl.² .......................................... C07D 239/95
[52] U.S. Cl. ...................... 260/256.5 R; 260/256.4 Q; 424/251
[58] Field of Search .................. 260/256.4 Q, 256.5 R

[56] References Cited

U.S. PATENT DOCUMENTS 3,867,384  2/1975  Bullock et al. ............... 260/256.5 R

OTHER PUBLICATIONS

Curd et al., J. Chem. Soc., (1974) pp. 775–790.

Primary Examiner—Paul M. Coughlan, Jr.
Attorney, Agent, or Firm—David M. Morse

[57] ABSTRACT

The quinazoline derivative having the formula

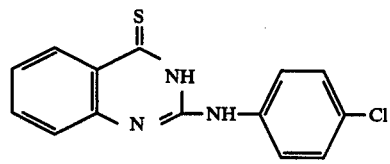

and pharmaceutically acceptable salts thereof are selective immunosuppressive agents useful in the treatment of immune complex diseases such as rheumatoid arthritis.

4 Claims, No Drawings

SELECTIVE IMMUNOSUPPRESSIVE AGENTS

BACKGROUND OF THE INVENTION

1. Field of the Invention

This invention relates to new therapeutically useful quinazoline derivatives, to processes for their preparation, to pharmaceutical compositions containing them and to methods of providing a selective immunosuppressive effect in the control or prophylaxis of immune complex diseases such as rheumatoid arthritis.

2. Description of the Prior Art

Evidence is accumulating that dysfunctional immune mechanisms play a major role in a number of diseases characterized by tissue damage. One group of such diseases is termed the immune complex diseases and includes such diseases as rheumatoid arthritis, juvenile rheumatoid arthritis, ankylosing spondylitis, psoriatic arthritis, Reiters syndrome, systemic lypus erythematosis, scleroderma, polymyositis, dermatomyositis, polyarteritis (including necrotizing arteritis), amyloidosis, Sjogren's syndrome, acute and chronic glomerulonephritis, autoimmune hemolytic anemia and relapsing polychondritis. Such chronic ailments are believed to involve a defect in host defense mechanisms which results in the formation of injurious immune complexes. These immune complexes set off a chain of events in the involved joint or tissue leading to inflammation, pain and, in severe circumstances, to disablement and even death.

Current drug therapy of rheumatoid arthritis is largely symptomatic, with primary emphasis on use of mild anti-inflammatory drugs, e.g. phenylbutazone, ibuprofen, naproxen, fenoprofen, etc. These compounds have little or no effect on the underlying disease which in many cases steadily progresses to the point of joint destruction. The use of potentially more effective agents such as the corticosteroids is limited by their severe side effects. Clearly there is a need for additional drugs for the treatment of rheumatoid arthritis which are effective and yet do not possess the serious adverse side effects of presently available agents. In particular, there is a need for drugs which are capable of inhibiting basic mechanisms underlying the initiation and progression of the disease and which are capable of arresting and even reversing the disease process.

As noted above, the immune complex group of diseases is believed to result from defects in the immune defense system. The immune defense system of a human or other warm-blooded animal is composed of two parts, both of which involve specialized lymphocytes which are stimulated to respond to an inciting antigen. One part, the cell-mediated (cellular immunity) arm, involving the direct participation of thymus dependent lymphocytes (T-cells), provides the major protection against intracellular pathogens, including a number of bacteria, most viruses, fungi and protozoa. It is also important in the transplantation rejection reaction and in the maintenance of a surveillance system for the elimination of cancer cells. The other part, the humoral (antibody-mediated) arm, involving thymus independent lymphocytes (B-cells) which can differentiate into antibody producing plasma cells, also plays an important role, especially in establishing long term immunity to many pathogens. A normal immune response results in the elimination of the offending antigen without tissue damage. In the immune complex diseases, however, there appears to be a breakdown in regulated antigen recognition such that antibodies (autoantibodies) and T-cells are produced which also react with altered components (antigens) of the host's own tissues producing immune complexes, with the resulting complexes leading to the tissue damage characteristic of these diseases.

A rational approach to the treatment of the immune complex diseases is to try to suppress the abnormal production of antibodies, i.e., to suppress the humoral immune response. Currently available immunosuppressive agents such as cyclophosphamide and azathioprine have been shown to be at least partially effective in treating rheumatoid arthritis and other immune complex diseases. These compounds, however, are capable of suppressing both the humoral and cellular immune responses, thus seriously impairing host resistance to infection and potentially increasing the risk of cancer.

It is an object of the present invention to make available a compound which will selectively suppress the humoral immune response believed primarily responsible for the immune complex diseases without suppressing or impairing the cellular immune response with its vital regulatory and host defense mechanism roles. It is a further object of the present invention to provide a selective immunosuppressant which will be effective in the prophylactic and therapeutic treatment of rheumatoid arthritis and other immune complex diseases. A further object is to provide such a selective immunosuppressant which is orally effective.

With respect to the novel quinazoline derivatives of the present invention, the prior art discloses the compounds 2-(4-chloroanilino)quinazolin-4(3H)-one (formula II below) and 2-(4-chloroanilino)-4-methylthioquinazoline (formula III) in *J. Chem. Soc.*, 775, (1947). No pharmacological utility is indicated for either compound.

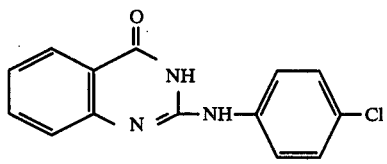

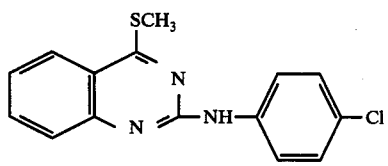

THE INVENTION

This invention relates to new therapeutically useful 2-anilinoquinazolin-4(3H)-thione derivatives, to processes for their preparation, to pharmaceutical compositions containing them and to methods for treating immune complex diseases in warm blooded animals by administration of such derivatives or pharmaceutical compositions. The compounds and compositions provided by the present invention selectively suppress the humoral immune response in a warm blooded animal and are useful in the prophylactic and therapeutic treatment of immune complex diseases.

More particularly, the present invention provides the novel immunosuppressive agent of the formula

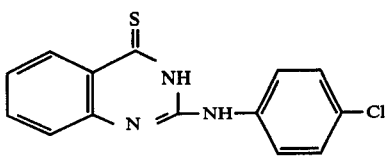

and its pharmaceutically acceptable salts. Compound I exists in both the thione and thiol tautomeric forms as indicated below:

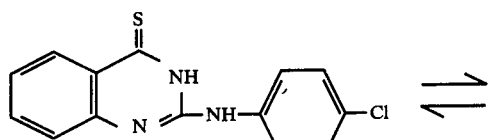

I-a
(Thione form)

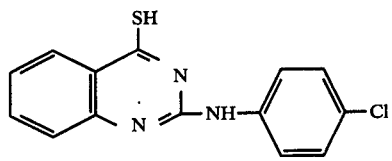

I-b
(Thiol form)

For convenience the subject compound will hereinafter and in the claims be represented only in the thione form, I-a, although it is understood that the thiol form of formula I-b is also included within the scope of the invention. Thus, reference below to compound "I" encompasses both tautomeric forms I-a and I-b.

The compound of the present invention is amphoteric and can thus form salts with both acids and bases. By "pharmaceutically acceptable salts" is meant salts with non-toxic organic or inorganic acids or bases. Examples of suitable acids include hydrochloric, hydrobromic, hydroiodic, nitric, sulfuric, methanesulfonic and 2-hydroxyethanesulfonic acids. Pharmaceutically acceptable salts may also be formed from strong bases such as the alkali metal hydroxides, e.g. NaOH or KOH, or alkaline earth metal hydroxides, e.g. Ca(OH)$_2$. Such pharmaceutically acceptable salts can be prepared according to known procedures by the reaction together of stoichiometric quantities of compound I and the appropriate acid or base with or without an appropriate solvent.

The compound of formula I may be prepared according to the preferred procedure by reacting 2-(4-chloroanilino)quinazolin-4(3H)-one (compound II below) with phosphorus pentasulfide according to the general method disclosed by R. N. Hurd and G. DeLaMater in *Chem. Reviews*, 61, 45 (1961) at page 47. The reaction may be expressed by the following scheme:

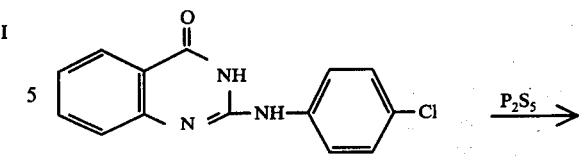

II

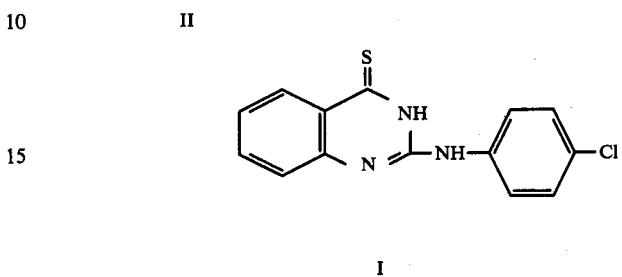

I

The above reaction may be carried out in the presence or absence of an inert organic solvent. Preferably, however, there is employed a reaction-inert organic solvent such as pyridine, carbon disulfide, hydrocarbons, e.g. benzene, xylene, toluene or tetrahydronaphthalene, or ethers such as tetrahydrofuran or dioxane. Although some reaction will occur no matter what proportion of reactants is employed, it is preferably in order to maximize yields to use stoichiometric amounts of compound II and P$_2$S$_5$ and, most preferably, an excess of the P$_2$S$_5$. Elevated temperatures are recommended for best results. When an inert solvent is employed, the reaction is preferably carried out at reflux temperature for a period of up to several hours. At the conclusion of the reaction the desired product may be recovered by extraction with an organic solvent (in the case where no solvent is employed) and/or adding water to the reaction mixture and collecting the insoluble compound I.

An alternate procedure for preparing compound I involves heating starting material II, aluminum trisulfide and a hydrated salt, e.g. Na$_2$SO$_4$.6H$_2$O, in a sealed tube. Enough sulfide and hydrate are used to insure that there is an excess of hydrogen sulfide present in the reaction mixture. This general reaction is described in *Ber.*, 54, 1079 (1921).

Still another alternative procedure for preparing compound I involves reacting starting material II with thioacetic acid at elevated temperatures, preferably reflux temperature, according to the general method disclosed in West German Pat. No. 943,227 [see also *Chem. Abstr.*, 53, 6262a (1959)].

Compound I may be converted by known methods to a pharmaceutically acceptable acid or base salt as mentioned above and such salts are equivalent to the free base for purposes of the present invention.

The selective immunosuppressive activity of compound I as its hydrochloride salt was demonstrated in the mouse by showing that the compound suppressed antibody formation (humoral immunity) at an oral dose of 3.1 mg./kg. while showing no suppression of cell-mediated immunity when administered orally at a dose of 100 mg./kg. Assessment of humoral immunity was made by measuring plaque forming cells from mouse spleen by the Jerne method described in *Science*, 140, 405 (1963) and *Nature*, 208, 858 (1965). Cell-mediated immunity was determined as a delayed type hypersensitivity response by measuring the swelling in mouse paws after challenge with purified protein derivative in the paws of Mycobacterium H37Ra-sensitized mice.

Compound I as its hydrochloride salt was also shown to be effective in suppressing arthritic symptoms both prophylactically and therapeutically when given orally in the rabbit immune synovitis model of rheumatoid arthritis which is considered to be a close animal model of human rheumatoid arthritis. [see *Fed. Proc.*, 32, 147 (1973); *J. Exptl. Pathol.*, 43, 373 (1962); and *Arthritis Rheum.*, 15, 327 (1972)].

In another aspect of the present invention, therefore, there is provided a method of selectively suppressing the humoral immune response in a warm-blooded animal which comprises administering to such an animal an effective dose of a compound of formula I or a pharmaceutically acceptable salt thereof.

The compounds of the present invention may be administered alone or in the form of pharmaceutical compositions, i.e. mixtures of the active compound with suitable pharmaceutical carriers or diluents. The compounds may be injected parenterally, but are preferably administered orally, for example in the form of tablets or capsules.

The compounds of the present invention are effective in suppressing the humoral immune response in warm-blooded animals at dosages in the range of about 1 to 100 mg./kg. of body weight. These values are illustrative only, however, and the physician of course will ultimately determine the dosage most suitable for a particular patient on the basis of factors such as the route of administration, age and weight of the patient and the particular disease being treated.

The following examples are provided solely for the purpose of illustrating preparation of the compounds of the present invention and are not to be construed as limitations of the invention. All temperatures referred to below are in degrees Centigrade.

EXAMPLE 1

2-(4-Chloroanilino)quinazoline-4(3H)-thione

A mixture of 2-(4-chloroanilino)quinazolin-4(3H)-one[(1)] (5.60 g., 0.0206 mole) and phosphorus pentasulfide (9.16 g., 0.0412 mole) in pyridine (75 ml.) was heated under reflux for 4 hours and then kept at 25° for 20 hours. The solution was poured into ice-water and the mixture stirred for 20 minutes. The mixture was filtered. The collected solid was washed with water and then recrystallized from 2-methoxyethanol: water to give the title compound (5.4 g., 91%), m.p. 264°–268°. Recrystallization from 2-methoxyethanol:water gave product with m.p. 268°–270°. 16 (1) F. H. S. Curd, J. K. Landquist, and F. L. Rose, *J. Chem. Soc.*, 775, (1947).

Anal. Calcd. for $C_{14}H_{10}ClN_3S$: C, 58.44; H, 3.50; Cl, 12.32; N, 14.60; S, 11.14. Found: C, 58.15; H, 3.55; Cl, 12.56; N, 14.77; S, 11.40.

EXAMPLE 2

2-(4-Chloroanilino)quinazoline-4(3H)-thione Hydrochloride

Concentrated hydrochloric acid (2 ml.) was added to a hot solution of 2-(4-chloroanilino)quinazoline-4(3H)-thione (1.5 g.) in 2-methoxyethanol (30 ml.). The precipitate was collected, washed with cold 2-methoxyethanol, and dried to give the title compound (1.6 g., 95%), m.p. 267°–274°.

Anal. Calcd. for $C_{14}H_{10}ClN_3S.HCl$: C, 51.87; H, 3.42; Cl, 21.87; N, 12.96; S, 9.89. Found: C, 52.10; H, 3.52; Cl, 21.67; N, 12.64; S, 10.15.

EXAMPLE 3

2-(4-Chloroanilino)quinazoline-4(3H)-thione, Sodium Salt

The title salt is prepared by treating 2-(4-chloroanilino)quinazoline-4(3H)-thione with at least a stoichiometric amount of aqueous sodium hydroxide and then lyophilizing the reaction mixture.

We claim:

1. The compound having the formula

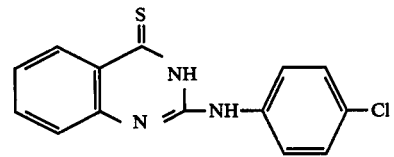

or a pharmaceutically acceptable salt thereof.

2. The compound having the formula

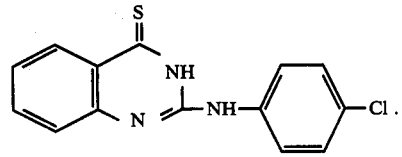

3. The hydrochloride salt of the compound of claim 2.

4. The sodium salt of the compound of claim 2.